(12) United States Patent
Weffers-Albu et al.

(10) Patent No.: US 12,076,161 B2
(45) Date of Patent: Sep. 3, 2024

(54) UNOBTRUSIVE SYMPTOMS MONITORING FOR ALLERGIC ASTHMA PATIENTS

(71) Applicant: KONINKLIJKE PHILIPS N.V., Eindhoven (NL)

(72) Inventors: Mirela Alina Weffers-Albu, Boukoul (NL); Rita Priori, Utrecth (NL); Declan Patrick Kelly, Shanghai (CN); Huibin Wei, Shanghai (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 338 days.

(21) Appl. No.: 17/129,275

(22) Filed: Dec. 21, 2020

(65) Prior Publication Data
US 2021/0196194 A1    Jul. 1, 2021

(30) Foreign Application Priority Data
Jan. 21, 2020    (EP) .................................... 20152921

(51) Int. Cl.
*A61B 5/00*    (2006.01)
*A61B 5/02*    (2006.01)
(Continued)

(52) U.S. Cl.
CPC .......... *A61B 5/4842* (2013.01); *A61B 5/0205* (2013.01); *A61B 5/02055* (2013.01);
(Continued)

(58) Field of Classification Search
CPC . A61B 5/4842; A61B 5/0205; A61B 5/02055; A61B 5/6824; A61B 5/6844;
(Continued)

(56) References Cited

U.S. PATENT DOCUMENTS

| | | | |
|---|---|---|---|
| 8,655,441 B2 | 2/2014 | Fletcher et al. | |
| 2006/0195035 A1* | 8/2006 | Sun ........................ | A61B 5/022 600/503 |

(Continued)

FOREIGN PATENT DOCUMENTS

| | | | |
|---|---|---|---|
| CA | 2766262 A1 * | 12/2010 | ............... A61B 5/02 |
| CN | 1903117 A | 1/2007 | |

(Continued)

OTHER PUBLICATIONS

Sumit Majumder et al, "Smartphone Sensors for Health Monitoring and Diagnosis", Sensors, May 2019.
(Continued)

*Primary Examiner* — Carl H Layno
*Assistant Examiner* — Manolis Pahakis

(57) ABSTRACT

The invention relates to a system and a method for providing an exacerbation risk score for a respiratory disease of a patient. The system measures a heart signal and/or a blood circulation signal of a patient and detects cough events and sneeze events in the measurement data. The cough events and sneeze events are indicative for an onset of a contagion and/or an allergy, which can rapidly exacerbate a respiratory disease of the patient. Thus, the system is configured for providing unobtrusively an exacerbation risk score to the patient and/or to a physician.

12 Claims, 5 Drawing Sheets

(51) Int. Cl.
  *A61B 5/0205* (2006.01)
  *A61B 5/021* (2006.01)
  *A61B 5/024* (2006.01)
  *A61B 5/08* (2006.01)

(52) U.S. Cl.
  CPC .......... *A61B 5/6824* (2013.01); *A61B 5/6844* (2013.01); *A61B 5/7267* (2013.01); *A61B 5/7275* (2013.01); *A61B 5/02028* (2013.01); *A61B 5/021* (2013.01); *A61B 5/02416* (2013.01); *A61B 5/0823* (2013.01); *A61B 5/411* (2013.01); *A61B 2562/0219* (2013.01)

(58) Field of Classification Search
  CPC . A61B 5/7267; A61B 5/7275; A61B 5/02028; A61B 5/021; A61B 5/02416; A61B 5/0823; A61B 5/411; A61B 2562/0219; A61B 2560/0247; A61B 5/02405; A61B 5/0295; A61B 5/681; G16H 50/20; G16H 50/30
  See application file for complete search history.

(56) References Cited

U.S. PATENT DOCUMENTS

| | | | |
|---|---|---|---|
| 2008/0243016 A1 | 10/2008 | Liao et al. | |
| 2011/0087079 A1* | 4/2011 | Aarts | A61B 7/003 600/300 |
| 2011/0112442 A1 | 5/2011 | Meger et al. | |
| 2012/0283581 A1* | 11/2012 | Olde | A61B 5/4094 600/485 |
| 2014/0350427 A1* | 11/2014 | Holder | A61B 5/0823 600/529 |
| 2015/0265787 A1* | 9/2015 | O'Connor | A61M 16/0875 128/204.23 |
| 2016/0331303 A1* | 11/2016 | Shen | A61B 5/7455 |
| 2019/0151585 A1* | 5/2019 | Troxell | A61B 5/087 |
| 2019/0167176 A1* | 6/2019 | Annoni | A61B 5/746 |
| 2020/0297955 A1* | 9/2020 | Shouldice | G16H 50/20 |
| 2021/0030276 A1* | 2/2021 | Li | A61B 5/0205 |
| 2021/0153773 A1* | 5/2021 | Wei | A61B 5/6802 |
| 2021/0196194 A1* | 7/2021 | Weffers-Albu | A61B 5/02055 |

FOREIGN PATENT DOCUMENTS

| | | | |
|---|---|---|---|
| EP | 3838137 A1 * | 6/2021 | .......... A61B 5/0022 |
| WO | 2017032873 A2 | 3/2017 | |

OTHER PUBLICATIONS

Hurst et al, "Epidemiological relationships between the common cold and exacerbation frequency in COPD", Eur Respir J 2005; 26: 846-852.

Tamer Elfaramawy et al., "Wireless Respiratory Monitoring and Coughing Detection Using a Wearable Patch Sensor Network", 2017, IEEE.

Nguyen, K. et al., "Cover Your Cough: Detection of Respiratory Events with Confidence Using a Smartwatch", Proceedings of Machine Learning Research 91:1-18, 2018.

John Allen, Photoplethysmography and its application in clinical physiological measurement, Physiol. Meas. 28 (2007) R1-R39, doi:10.1088/0967-3334/28/3/R01.

"Does Your Heart Stop for an Instant When You Sneeze?", https://uamshealth.com/medical-myths/does-your-heart-stop-for-an-instant-when-you-sneeze/, Mar. 2019, UAMS Health.

International Search Report and Written Opinion, International Application No. PCT/EP2020/087589, Mailed on Mar. 4, 2021.

* cited by examiner

UNOBTRUSIVE SYMPTOMS MONITORING FOR ALLERGIC ASTHMA PATIENTS

CROSS-REFERENCE TO PRIOR APPLICATIONS

This application claims the benefit of European Patent Application No. 20152921.1, filed on 21 Jan. 2020 and International Application No. PCT/CN2019/128293, 25 Dec. 2019. This application is hereby incorporated by reference herein.

FIELD OF THE INVENTION

The present invention relates to a system for providing an exacerbation risk score for a respiratory disease of a patient, and a method for providing an exacerbation risk score for a respiratory disease of a patient.

BACKGROUND OF THE INVENTION

The condition of patients with a respiratory disease like asthma can rapidly exacerbate in the presence of a cold or a flu as well as when prompted by an allergic reaction.

Asthma exacerbations are potentially fatal and often the exacerbations triggered by infections are the most serious. Determining the symptoms associated with the onset of a contagion or an allergy at an early stage is crucial in combating them, and thereby preventing the deterioration of the patient respiratory function due to exacerbations of the respiratory disease triggered by the afore-mentioned factors. Early detection of an allergic reaction and cold or flu symptoms can warn the user and allow them to take action, specifically to take their regular medicine. Most patients do not take their medicine all the time but only take it when they perceive a need. An early warning can indicate the need before the patient is aware of asthma symptoms, and can contribute to ensure that the patients have their reliever medication with them. For children, this warning to the parent can help them to manage their child's asthma effectively. In general, there is no method available in the state of the art that reliably predicts asthma exacerbations in daily life of a patient.

Solutions such as monitoring exhaled breath or expiratory peak flow are not used in practice due to the perceived burden on the patient.

US 2019/0167176 A1 discloses a system for monitoring and treating respiratory distress in a patient including signal inputs, a signal processing unit, and a respiratory distress analyzer. For these reasons, it would be advantageous to have a system and a method for providing an exacerbation risk score for a respiratory disease of a patient that does not suffer from the above-mentioned drawbacks.

SUMMARY OF THE INVENTION

It is an object of the present invention to provide a system and a method for providing an exacerbation risk score for a respiratory disease of a patient, which monitors unobtrusively the symptoms of an allergic reaction or a contagion like a cold or a flu.

The object of the present invention is solved by the subject matter of the independent claims, wherein further embodiments are incorporated in the dependent claims.

The described embodiments similarly pertain to the system and the method for providing an exacerbation risk score for a respiratory disease of a patient. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The herein presented methods can be carried out with another order of the disclosed steps without departing from the respective method embodiment, unless explicitly mentioned to the contrary hereinafter.

According to a first aspect of the invention, there is provided a system for providing an exacerbation risk score for a respiratory disease of a patient. The system comprises a measurement unit configured for measuring a heart signal and/or a blood circulation signal of a patient and configured for providing corresponding measurement data. The system comprises a detection unit configured for receiving the measurement data and for detecting a cough event and/or a sneeze event of the patient in the measurement data. The system comprises a calculation unit configured for calculating an exacerbation risk score for a respiratory disease of the patient based on the detected cough event and/or the detected sneeze event and an interface unit configured for providing the exacerbation risk score to the patient and/or to a physician.

The system determines the patient risk of exacerbation of a respiratory disease by monitoring symptoms such as coughing and sneezing signaling an onset of contagion and/or an allergy. The symptoms like coughing and sneezing are derived from a measurement of a heart signal and/or a blood circulation signal. These can be unobtrusively measured with a measurement unit attached to the body of the patient. The cough event and/or the sneeze event can be an indicator of an upcoming infection or allergy. A detection unit is configured for receiving measurement data corresponding to the heart signal and/or the blood circulation signal form the measurement unit and for detecting a cough event and/or a sneeze event in the measurement data. A calculation unit calculates an exacerbation risk score indicating the risk for a deterioration of the respiratory disease of the patient based on the detected cough and/or sneeze events. The exacerbation risk score can be used to update an existing value of an exacerbation risk score acquired in a previous measurement. An interface unit is configured for providing the exacerbation risk score to the patient. Alternatively or in addition, the exacerbation risk score can be provided to a care person if the patient, which may be a physician or the parents in case the patient is a child.

In an embodiment of the invention, the blood circulation signal comprises at least on of: blood pressure, blood volume, and blood flow.

The blood circulation signal comprises a blood pressure, a blood volume, or a blood flow. In addition, a combination thereof is possible. The heart signal can correspond to the frequency or the amplitude of the heart beats.

In an embodiment of the invention, the measurement unit is a wearable unit such as a bracelet comprising a first sensor for measuring the heart signal and/or the blood circulation signal.

The measurement unit can be a wearable device like a bracelet or a wristband comprising a sensor. It can be worn around the wrist of the patient, or it can be fixed to another part of the body of the patient. Wristbands measuring vital signs of a patient are acceptable to the patient and provide an unobtrusive way for measuring the heart signal and a blood circulation signal of the patient both during daytime and during nighttime.

In an embodiment of the invention, the first sensor is a photoplethysmographic sensor.

The sensor of the measurement unit can be a photoplethysmographic sensor. This sensor can comprise a light source to illuminate a part of the body of the patient, preferably the skin, and a photodetector, which measures the light reflected from the skin. The reflected light is influenced by the amount of blood circulating in the skin. Changes of the amount of blood in the skin can be due to a heartbeat or a change of the blood pressure, for example.

In an embodiment of the invention, the respiratory disease is asthma or chronic obstructive pulmonary disease.

The respiratory disease of the patient can be asthma or chronic obstructive pulmonary disease. Further, an exacerbation risk score for any other disease can be provided, which can deteriorated in the presence of, for example, an allergic reaction or a contagion like a flu or a cold.

In an embodiment of the invention, the detection unit is configured for detecting the cough event by analyzing an inter-beat interval of the heart signal.

The detection unit can rely on changes in the inter-beat interval of the heart signal to detect a cough event. The inter-beat interval can be defined as the time elapsing between two subsequent systolic phases of the heart signal, i.e. the time between two heartbeats.

In an embodiment of the invention, the detection unit is configured for detecting the cough event by a fluctuation of the length of the inter-beat interval over a plurality of heartbeats.

The cough detection algorithm of the detection unit can rely on the observation that during a cough event the heart sinus of the heart signal measured with a photoplethysmographic sensor can be significantly disrupted. Therefore, the inter-beat interval is significantly fluctuating as well, and can be used for determining a cough event.

In addition, the cough detection algorithm can ensure that the detected changes in the heart sinus are due to a cough event and not to other artefacts such as a relative movement of the photodetector or the light generating source of the sensor with respect to the skin. The cough detection algorithm can make use of a patient specific reference inter-beat interval learned by the detection unit at rest of the patient. This reference inter-beat interval can be learned by the detection unit at system initialization, or during run time by adding an accelerometer to the system to identify a patient resting state while measuring the reference inter-beat interval. A Further, the detection unit can monitor that a good contact of the sensor to the skin is ensured. A skin-sensor contact can be maintained and a quality check can be performed and tracked by means of a quality indicator.

In an embodiment of the invention, the detection unit is configured for detecting the sneeze event by analyzing a heart rate of the heart signal and a blood pressure of the blood circulation signal.

The detection unit can rely on a change in the heart rate of the heart signal and a change of the blood pressure of the blood circulation signal to detect a sneeze event. The heart rate can be defined as the number of heartbeats per time unit. The blood pressure can also be derived from a blood volume or a blood flow flowing through the skin of the patient.

In an embodiment of the invention, the detection unit is configured for detecting the sneeze event by a decreasing heart rate in temporal correlation with an increasing blood pressure.

The algorithm for sneeze detection can rely on the physiologic reaction of the body of the patient that when the patient sneezes, the intrathoracic pressure in the body can momentarily increase. This can decrease the blood flow back to the heart. The heart compensates for this by changing its regular heartbeat momentarily to adjust. Sneeze events detection can be performed by correlating an abrupt decrease of the heart rate and a rise in the blood pressure.

In an embodiment of the invention, the system is configured for storing a record of exacerbation risk score values of the patient and for providing the record to the patient and/or to the physician.

A record of exacerbation risk scores can be stored and a trend of the risk scores can be provided. Further, the system can provide a signal to the patient, in case the exacerbation risk score is updated, specifically if the exacerbation risk score is increased with respect to a precedent measurement of the exacerbation risk score.

In an embodiment of the invention, the system comprises a second sensor configured for detecting skin contact, temperature, and/or acceleration.

This second sensor can be used for verification of the detected signals from the heart and the blood circuit. The skin contact sensor can detect whether the first sensor has a good contact to the skin, thereby ensuring that only measurement data are used for cough and sneeze detection, when the first sensor has good contact to the skin and provides reliable measurement data. The temperature sensor can be used to measure the temperature of the skin, and thus a contact of the first and second sensors to the skin can be monitored. An acceleration sensor can be used to verify detected cough events and sneeze events, as cough and sneeze events have an influence to the motion of the body. In addition or as an alternative to an involuntary movement of the body caused by the cough event or the sneeze event, the patient can use their hand to cover the mouth, which results in a characteristic acceleration signal of the acceleration sensor, which can be used to verify the occurrence of a cough or sneeze event.

In an embodiment of the invention, the calculation unit comprises an artificial intelligence module configured for being trained with data from a plurality of patients in order to predict the exacerbation risk score.

The exacerbation risk score can be calculated based on a frequency of the detected cough and sneeze events. The increase or decrease of the score value can be done based on learning on population data. The data concerning the occurrence of cough and sneeze events of the patient collected as described above can be combined with other data that indicate exacerbations and potentially severity of the respiratory disease. For example, patients with connected reliever inhalers will take their reliever inhaler one or more times in case of an exacerbation and the number of repetitions and a corresponding frequency is an indicating of the severity of the exacerbation. Emergency room visits or hospital admissions and the related physician evaluation can indicate a severity of the exacerbation. Taking the data from a subset of the population where there is additional data on exacerbations allows the system as according to the invention to use machine learning methods to train a model to predict exacerbation risk based on the detected cough and sneeze events. This machine learning training can ensure that the patterns that indicate oncoming exacerbations are separated from isolated coughs/sneezes. After using machine learning on the subset of the population with additional data concerning the occurrence of cough or sneeze events and a corresponding exacerbation risk score, the calculation of an exacerbation risk score can be applied to the every patient of a complete population. The exacerbation risk score can also be personalized based on the individual situation of the patient. For instance, if one is known to be allergic to certain pollen, then during corresponding season, the same frequency of cough/sneeze would be evaluated as a higher exacerbation risk score than during another season, since the chance of exacerbation of the respiratory disease to be triggered by pollen can be higher. Another scenario could be that in days with bad air quality, i.e. unhealthy air quality for a sensitive group of patients, the detection of frequent cough/sneeze events would also cause more attention on the exacerbation risk by rating a higher score than on days with good air quality.

According to another aspect of the invention, there is provided a method for providing an exacerbation risk score for a respiratory disease of a patient. The method comprises the steps of measuring a heart signal and/or a blood circulation signal of a patient and providing corresponding measurement data. The method comprises further the steps of detecting a cough event and/or a sneeze event of the patient based on the measurement data and calculating an exacerbation risk score for a respiratory disease of the patient based on the detected cough event and/or the detected sneeze event. The method comprises further the step of providing the exacerbation risk score to the patient and/or to physician.

The method according to the invention provides an exacerbation risk score for a respiratory disease of a patient. In a first step, a heart signal and/or a blood circulation signal of a patient is measured and corresponding measurement data are provided. In the second step, a cough event and/or a sneeze event of the patient is detected based on the measurement data. In the third step, an exacerbation risk score for a respiratory disease of the patient is calculated based on the detected cough event and/or the detected sneeze event. In the fourth step, the exacerbation risk score is provided to the patient and/or to a physician.

According to another aspect of the invention, there is provided a computer program element, which, when executed on a processing unit, instructs the processing unit to perform the method according to the preceding aspect of the invention.

The computer program element can be performed on one or more processing units, which are instructed to perform the method for providing an exacerbation risk score for a respiratory disease of a patient when the computer program element is executed.

According to another aspect of the invention, there is provided a processing unit configured for executing the computer program element according to the preceding aspect of the invention.

The processing unit can be, for example, a processor of a communication device like a telephone, a smartphone, a tablet, a smart watch, bracelet, or smart glasses. The processing unit can also be distributed over one or more different devices, such that a part of the computer program element can be executed on the communication device, and another part, for example, on a server. The bracelet can be communicationally connected to the communication device, and an application installed on the communication device can be configured for performing the steps of the method according to the invention.

Thus, the benefits provided by any of the above aspects equally apply to all of the other aspects and vice versa.

In a gist, the invention relates to a system and a method for providing an exacerbation risk score for a respiratory disease of a patient. The system measures a heart signal and/or a blood circulation signal of a patient and detects cough events and sneeze events in the measurement data. The cough events and sneeze events are indicative for an onset of a contagion and/or an allergy, which can rapidly exacerbate a respiratory disease of the patient. Thus, the system is configured for providing unobtrusively an exacerbation risk score to the patient and/or to a physician.

The above aspects and embodiments will become apparent from and be elucidated with reference to the exemplary embodiments described hereinafter. Exemplary embodiments of the invention will be described in the following with reference to the following drawings:

DETAILED DESCRIPTION OF EMBODIMENTS

Figure 1:
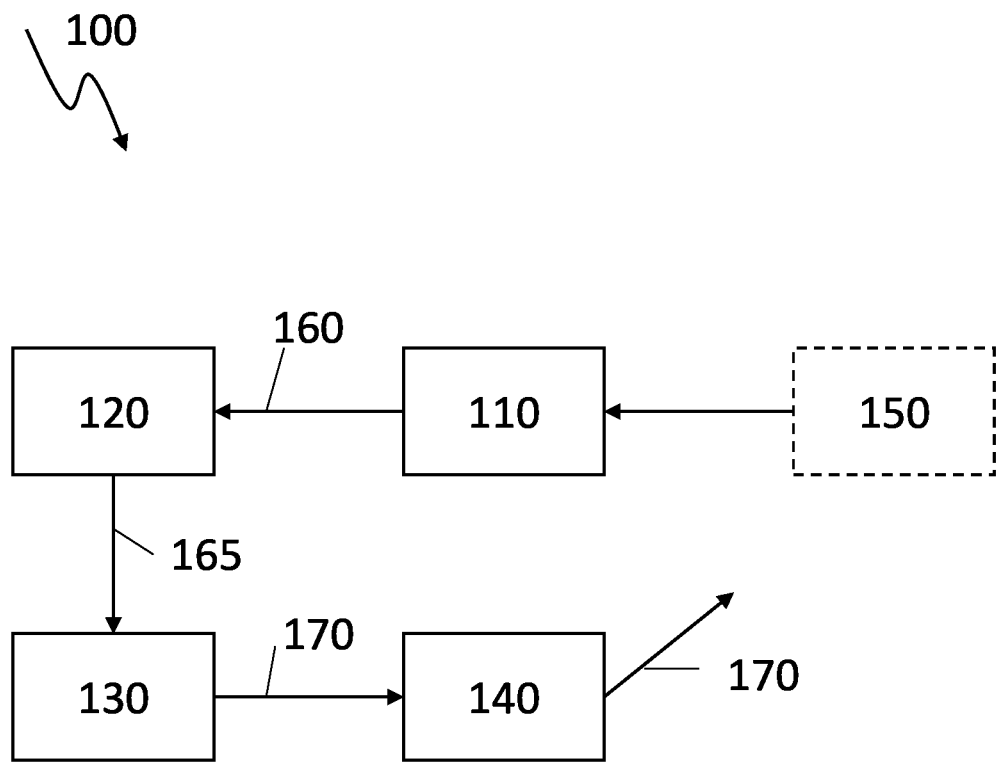
FIG. 1 shows a schematic set-up of a system for providing an exacerbation risk score for a respiratory disease of a patient according to a first embodiment of the invention.

FIG. 1 shows a schematic set-up of a system 100 for providing an exacerbation risk score 170 for a respiratory disease of a patient 150 according to a first embodiment of the invention. A measurement unit 110 measures a heart signal and/or a blood circulation signal of a patient 150. Measurement data 160 corresponding to the heart signal and/or the blood circulation signal are provided and received by the detection unit 120. The detection unit 120 is configured for detecting a cough event and/or a sneeze event 165 of the patient 150 in the measurement data 160. The calculation unit 130 is configured for calculating an exacerbation risk score 170 for the respiratory disease of the patient. This exacerbation risk score 170 is provided by the interface unit 140 to the patient 150 and/or to a physician.

Figure 2:
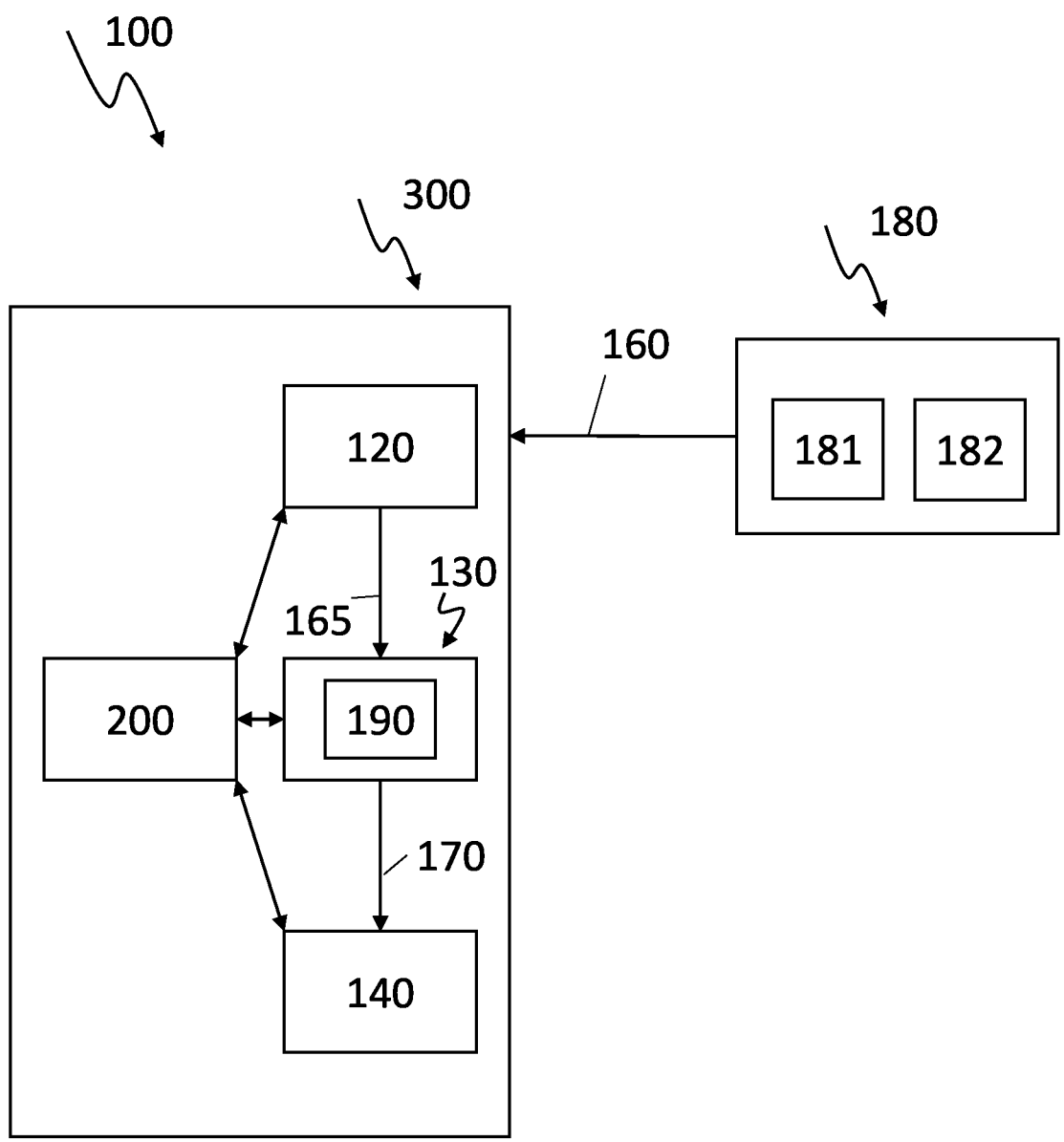
FIG. 2 shows a schematic set-up of a system for providing an exacerbation risk score for a respiratory disease of a patient according to a second embodiment of the invention.

FIG. 2 shows a schematic set-up of a system 100 for providing an exacerbation risk score 170 for a respiratory disease of a patient 150 according to a second embodiment of the invention. In this embodiment of the invention, the measurement unit 110 is a wearable device 180 comprising a first sensor 181 and a second sensor 182. The first sensor 181 is configured for measuring the heart signal and/or the blood circulation signal of the patient 150. The second sensor 182 is configured for measuring the skin contact and thus provides data regarding the reliability of the data measured by the first sensor 181. The measurement data 160 are transmitted to a communication device 300 like a smartphone, a tablet, a smartwatch, smart glasses, etc. However, the wearable device 180 can be, for example, the smartwatch, or the wearable device 180 can comprise the detection unit 120, the calculation unit 130 and the interface unit 140. The communication device comprises in this embodiment of the invention the detection unit 120 for receiving the measurement data 160 and for detection a cough event and/or a sneeze event 165. These are provided to the calculation unit 130, which can comprise an artificial intelligence module 190 trained for providing the exacerbation risk score 170. The exacerbation risk score 170 is provided by the interface unit 140 to the patient 150 and/or top a physician. A processing unit 200 can be communicationally connected to the detection unit 120, the calculation unit 130 and the interface unit 140, and can be configured for controlling the detection unit 120, the calculation unit 130 and the interface unit 140 and for executing the steps of the method according to the invention.

Figure 3:
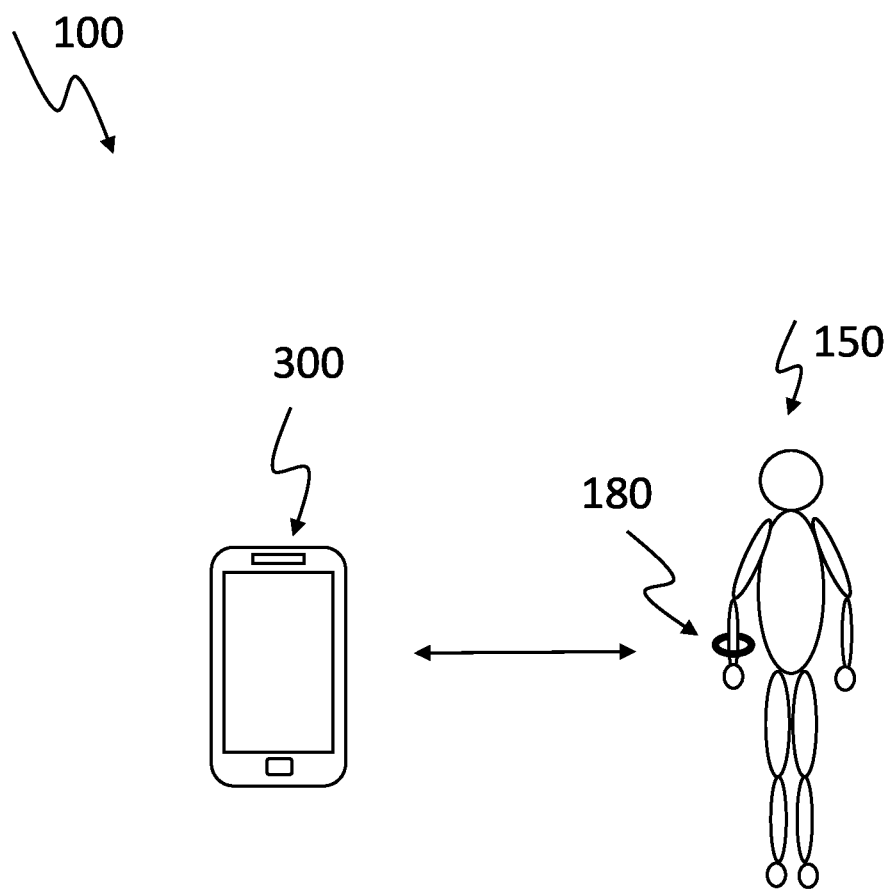
FIG. 3 shows a schematic set-up of a system for providing an exacerbation risk score for a respiratory disease of a patient according to a third embodiment of the invention.

FIG. 3 shows a schematic set-up of a system 100 for providing an exacerbation risk score 170 for a respiratory disease of a patient 150 according to a third embodiment of the invention. A wearable unit 180 is attached to the wrist of a patient 150. The wearable unit 180 can be communicationally connected to a communication device 300, for example by a wireless connection like WLAN or Bluetooth.

Figure 4:
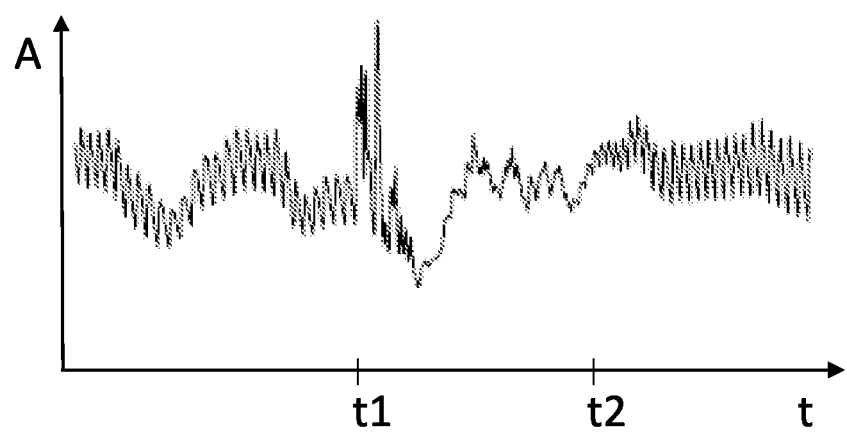
FIG. 4 shows the heart signal of a patient measured by the measurement unit during a cough event of the patient.

FIG. 4 shows the heart signal of a patient 150 measured by the measurement unit 110 during a cough event 165 of the patient 150. The amplitude A of a signal measured by the measurement unit 110 shows usually in case of no cough events and/or sneeze events a regular, sinus-like waveform measured over time t. In the time interval starting at t1 and ending at t2, a cough event 165 is detected due to a disruption of the regular waveform with a significantly fluctuating inter-beat interval.

Figure 5:
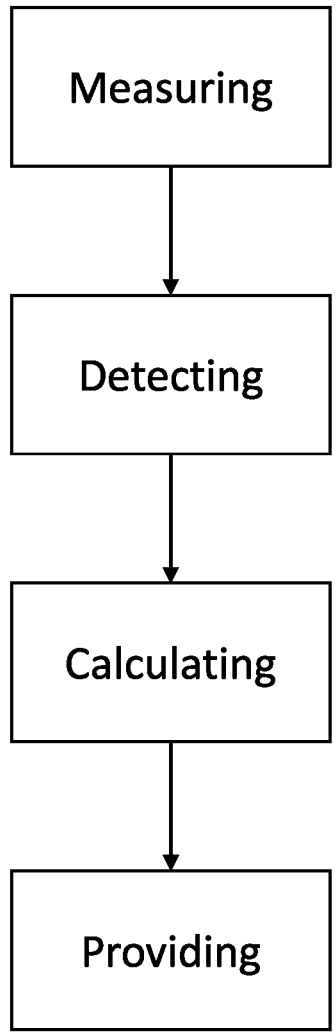
FIG. 5 shows a block diagram of a method for providing an exacerbation risk score for a respiratory disease of a patient according to an embodiment of the invention.

FIG. 5 shows a block diagram of a method for providing an exacerbation risk score 170 for a respiratory disease of a patient 150 according to an embodiment of the invention. The method comprises a first step of measuring a heart signal and/or a blood circulation signal of a patient and providing corresponding measurement data 160. This step is followed by a second step of detecting a cough event and/or a sneeze event 165 of the patient 150 based on the measurement data 160. The third step comprises calculating an exacerbation risk score 170 for a respiratory disease of the patient 150 based on the detected cough event and/or the detected sneeze event 165. In the fourth step, the exacerbation risk score 170 is provided to the patient 150 and/or to a physician.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

The invention claimed is:

1. A system for assisting with treatment of a respiratory disease of a patient by providing an exacerbation risk score for the respiratory disease, the system comprising:
   a measurement unit configured for measuring a heart signal and/or a blood circulation signal of a patient, and configured for providing corresponding measurement data;
   a processing unit configured for:
   (i) receiving the measurement data and for detecting a cough event and/or a sneeze event of the patient in the measurement data,
      wherein the processing unit is configured for detecting the cough event by analyzing an inter-beat interval of the heart signal, and
      wherein the processing unit is configured for detecting the sneeze event by analyzing a heart rate of the heart signal and a blood pressure of the blood circulation signal;
   (ii) calculating an exacerbation risk score for the respiratory disease of the patient based on the detected cough event and/or the detected sneeze event, wherein the processing unit comprises a trained artificial intelligence machine learning module that is trained to automatically predict exacerbation risk using patterns that indicate oncoming exacerbations that are separated from isolated coughs and/or sneezes; and
   (iii) providing the exacerbation risk score to the patient and/or to a physician.

2. The system according to claim 1,
   wherein the blood circulation signal comprises at least on of: blood pressure, blood volume, and blood flow.

3. The system according to claim 1,
   wherein the measurement unit is a wearable unit such as a bracelet comprising a first sensor for measuring the heart signal and/or the blood circulation signal.

4. The system according to claim 3, wherein the first sensor is a photoplethysmographic sensor.

5. The system according to claim 1, wherein the respiratory disease is asthma or chronic obstructive pulmonary disease.

6. The system according to claim 1, wherein the processing unit is configured for detecting the cough event by a fluctuation of the length of the inter-beat interval over a plurality of heartbeats.

7. The system according to claim 1, wherein the processing unit is configured for detecting the sneeze event by a decreasing heart rate in temporal correlation with an increasing blood pressure.

8. The system according to claim 1,
   wherein the system is configured for storing a record of exacerbation risk score values of the patient and for providing the record to the patient and/or to the physician.

9. The system according to claim 1,
   wherein the system comprises a second sensor configured for detecting skin contact, temperature, and/or acceleration.

10. A computer-implemented method for assisting with treatment of a respiratory disease of a patient by providing an exacerbation risk score for the respiratory disease, the computer-implemented method comprising the steps of:
   measuring a heart signal and/or a blood circulation signal of a patient and providing corresponding measurement data;
   detecting a cough event and a sneeze event of the patient based on the measurement data;
      wherein the cough event is detected by analyzing an inter-beat interval of the heart signal, and
      wherein the sneeze event is detected by analyzing a heart rate of the heart signal and a blood pressure of the blood circulation signal;
   calculating an exacerbation risk score for a respiratory disease of the patient based on the detected cough event and/or the detected sneeze event using a processing unit, wherein the processing unit comprises a trained artificial intelligence machine learning module that is trained to automatically predict exacerbation risk using patterns that indicate oncoming exacerbations that are separated from isolated coughs and/or sneezes; and
   providing the exacerbation risk score to the patient and/or to a physician.

11. A computer program element comprising a non-transitory computer usable medium having a computer readable program code embodied therein, which, when executed on a processing unit, instructs the processing unit to cause the system of claim 1 to perform a method for assisting with treatment of a respiratory disease of a patient by providing an exacerbation risk score for the respiratory disease, the method comprising the steps of:

measuring a heart signal and/or a blood circulation signal of a patient and providing corresponding measurement data;

detecting a cough event and a sneeze event of the patient based on the measurement data,
    wherein the cough event is detected by analyzing an inter-beat interval of the heart signal, and
    wherein the sneeze event is detected by analyzing a heart rate of the heart signal and a blood pressure of the blood circulation signal;

calculating an exacerbation risk score for a respiratory disease of the patient based on the detected cough event and/or the detected sneeze event using a processing unit, wherein the processing unit comprises a trained artificial intelligence machine learning module that is trained to automatically predict exacerbation risk using patterns that indicate oncoming exacerbations that are separated from isolated coughs and/or sneezes; and providing the exacerbation risk score to the patient and/or to a physician.

12. A processing unit configured for executing the computer program element according to claim 11.

* * * * *